United States Patent [19]

Barger

[11] Patent Number: 5,763,729
[45] Date of Patent: Jun. 9, 1998

[54] ALKYLATION OF ALKANES WITH ALKYL HALIDES

[75] Inventor: Paul T. Barger, Arlington Heights, Ill.

[73] Assignee: UOP, Des Plaines, Ill.

[21] Appl. No.: 694,015

[22] Filed: Aug. 8, 1996

Related U.S. Application Data

[63] Continuation-in-part of Ser. No. 337,782, Nov. 14, 1994, abandoned.

[51] Int. Cl.$^6$ .............. C07C 2/58; B01J 23/40; B01J 23/50; B01J 23/02
[52] U.S. Cl. .............. 585/728; 585/721; 585/727; 502/327; 502/328; 502/330; 502/304; 502/340; 502/341; 502/344; 502/347; 502/348
[58] Field of Search .............. 585/721, 727, 585/728; 502/327, 328, 330, 304, 340, 341, 344, 347, 348

[56] References Cited

U.S. PATENT DOCUMENTS

| 2,882,324 | 4/1959 | Schmerling | 585/728 |
| 2,999,074 | 9/1961 | Bloch et al. | 502/227 |

*Primary Examiner*—Glenn Caldarola
*Assistant Examiner*—In Suk Bullock
*Attorney, Agent, or Firm*—Thomas K. McBride; Eugene I. Snyder

[57] ABSTRACT

Although olefins commonly are used to alkylate alkanes using various solid acid catalysts, the process is severely hampered by short catalyst lifetimes attending substantial olefin oligomerization. This problem can be avoided by using an alkyl chloride as the alkylating agent. Thus, alkylation of isobutane by olefin in the presence of a modified, AlCl$_3$-type Friedel-Crafts catalyst at 30°C falls to about 77% in four hours, whereas alkylation with sec-butyl chloride at the same conditions fell to 88% over 30 hours.

12 Claims, 1 Drawing Sheet

ALKYLATION OF ALKANES WITH ALKYL HALIDES

CROSS REFERENCE TO RELATED APPLICATIONS

This application is a continuation-in-part of application Ser. No. 08/337,782, now abandoned, filed Nov. 14, 1994 all of which is hereby incorporated by reference.

1. Field of the invention

This invention relates to the alkylation of lower alkanes with lower alkyl halides to afford other alkanes, principally in the C5–C12 range, suitable for use as a motor fuel. In particular, it relates to modification of the alkylation process to substantially increase catalyst lifetime and to decrease concomitant olefin oligomerization.

BACKGROUND OF THE INVENTION

Even in the era of anti-knock additives such as tetraethyl lead, the use of alkylate as a component in motor fuel gained both universal acceptance and importance. In the ensuing years alkylate has become an even more important component of motor fuel. Alkylate is an economical, clean-burning, high-octane, low volatility product that is becoming increasingly important as the composition of gasoline changes in response to environmental concerns and legislation. The governmental regulations most applicable to the increasing importance of alkylates are those affecting lead and butane. Adding lead anti-knock compounds was the easiest way to raise gasoline octane, but because of continuing concerns over the effects of lead emissions the phasing out of lead in gasoline was required, a process over 90% complete. Butane is another effective octane-booster but tends to evaporate from gasoline, especially in warm weather, contributing to smog formation. Recent EPA regulations have effected their virtually complete removal from gasoline.

The term "alkylate" generally refers to a complex mixture resulting from the alkylation of C2–C6 alkenes (olefins) present or formed in a feedstream with intermediates arising primarily from alkanes, especially branched alkanes, and predominantly those with 4 carbon atoms, especially isobutane, also present in the same feedstream. It is most desirable that the complex product mixture from C4 alkenes and alkanes, referred to as alkylate, contains predominantly trimethylpentanes, since these are high-octane components which add considerable value to motor fuel, yet the chemistry of alkylation affords a dazzling variety of products resulting from only a few basic chemical reactions characteristic of the carbocations, the species which plays a central role in the alkylation process. Thus, chemical processes as chain transfer (intermolecular hydride transfer and alkyl shifts), oligomerization and disproportionation serve to place into the alkylate, as byproduct, materials of from 5–12+ carbon atoms from a feed containing only C4 alkenes and C4 alkanes.

The alkylation of alkenes is catalyzed by strong acids generally. Although such alkylation has been the focus of intense and continuing scrutiny for several decades, the requirements of optimum selectivity while achieving high conversion have heretofore narrowed, for all practical purposes, the commercial choice of catalyst to sulfuric acid and liquid hydrogen fluoride. While processes based on each of these acids have gained commercial acceptance those based on HF have been favored at least in part because of the relative ease of HF regeneration. A brief but valuable overview of HF-catalyzed alkylation is presented by B.R. Shah in "Handbook of Petroleum Refining Processes", R.A. Meyers, editor, McGraw-Hill Book Company, 1986, pp 1-3 through 1-28.

In a rather over-simplified description, the HF-catalyzed alkylation process is carried out as follows. Alkene and isobutane feedstocks are combined and mixed with HF in an alkylation reaction zone. The reactor effluent is separated into the desired alkylate, acid, and other light gases which are predominantly unreacted isobutanes. The HF is either recycled to the reactor directly or regenerated, in whole or in part, prior to its being recycled to the reactor. Unreacted isobutane also is recycled to the reactor, and the alkylate is then used in motor fuel blending.

Recently HF (hydrofluoric acid) has come under environmental pressure. Hydrofluoric acid is classified as an Acutely Hazardous Material, and in Southern California the Board of the South Coast Air Quality Management District recently required that the use of HF in alkylation be phased out by Jan. 1, 1998. Consequently there is increasing reason to seek substitutes for HF as an alkylation catalyst for alkylate production. It is quite desirable to have a solid acid as an effective catalyst, for this permits development of fixed bed processes, a desirable alternative in the petroleum refining industry.

In response to environmental sensitivity to hydrogen fluoride a spate of solid acid catalysts has been suggested as alternative alkylation catalysts, especially Lewis acids such as aluminum halides, boron trifluorides, antimony pentafluoride, and so forth, and modified or supported Bronsted acids such as sulfated zirconia. In all processes heretofore suggested the solid acid alkylation catalysts have been used in conjunction with alkenes. Although traditional and conventional alkylation to form alkylate of interest as a motor fuel employs the reaction between alkanes and alkenes, such alkylation processes are encumbered by serious disadvantages when solid acids are used as the catalyst. In particular, the foregoing alkylation process always is accompanied by oligomerization of alkenes, which also is an acid-catalyzed reaction, and the relative amount of oligomerization increases drastically when a solid acid is used as the alkylation catalyst relative to the use of, for example, HF as the alkylation catalyst. The traditional alkylation process catalyzed by a solid acid catalyst also is plagued by limited stability of the catalyst; lifetimes under about 6 hours are common.

Thus there are two problems to be overcome in solid bed alkylation process using an alkane-alkene mixture; oligomerization of the alkene and a short catalyst lifetime. One solution to this problem is to conduct alkylation at a very high alkane to alkene ratio, say >100:1. However, such a high ratio is impractical because it requires a very large recycle stream and because of the increased reactor size required for a given productivity (e.g., as measured by alkylate formed per hour). We conjectured that substitution of an alkene by an alkyl halide might provide results equivalent to a very high alkane/alkene ratio. In fact our speculations proved correct and led to the instant invention. Thus, we discovered that substitution of an alkene by an alkyl halide in solid catalyst-mediated alkylation substantially decreased olefin oligomerization attending alkylation and, even more importantly, substantially increased catalyst stability as measured by catalyst life.

There appears to be little relevant to our discovery in the prior art. U.S. Pat. No. 3,585,252 describes the preparation of alkylate by coupling alkyl halides with organoaluminum compounds, especially trialkylaluminum compounds. In U.S. Pat. No. 4,229,611 the patentee describes the use of a strong Lewis acid system to catalyze the alkylation reaction between alkyl halides and alkenes. The use of clays to convert C1–C4 monohaloalkanes into hydrocarbons of a higher carbon number than the individual reactants is described in U.S. Pat. No. 4,579,996. The clays used contain hydrogen ions and/or metal cations introduced by exchange or deposition, and the use of pillared layered clays is preferred.

U.S. Pat. No. 2,882,324 describes alkylation of hydrocarbons using as a catalyst a mixture of an aluminum halide, a titanium oxide, and an alkali or alkaline earth metal or aluminum. The patentee there speculates that alkyl halides may be used as alkylating agents, although not necessarily with equivalent results, since there is accompanying consumption of the metallic portion of the catalyst (i.e., alkali, alkaline earth metal, or aluminum). The patentee of U.S. Pat. No. 3,976,714 teaches a catalyst consisting essentially of graphite having intercalated therein a Lewis acid, including aluminum chloride, and teaches the catalyst as effective in alkylation of alkylatable hydrocarbons with an olefin, alcohol, or alkyl halide. It is critical to note that neither of these teaches the catalyst of our invention or the particular feedstocks of our invention. Even more importantly, neither recognizes that substitution of olefin by alkyl halide decreases oligomerization products and substantially increases catalyst lifetime, both of which are cornerstones of our invention.

SUMMARY OF THE INVENTION

The purpose of this invention is to prepare alkylate in the C5–C12+ range, suitable as a motor fuel, by solid catalyst-mediated alkylation of alkanes with reduced oligomer production and increased catalyst life. An embodiment is the reaction of alkyl halides containing between 3 and about 5 carbon atoms with alkanes containing from about 4 up to about 6 carbon atoms in the presence of a solid acid catalyst which is a metal halide bound to surface hydroxyl groups of a refractory inorganic oxide as modified by the presence of a second but unbound metal halide. In a more specific embodiment the alkanes are branched alkanes. In another specific embodiment the alkyl halides are secondary or tertiary alkyl halides. In yet another specific embodiment the alkyl halide is sec-butyl chloride or tert-butyl chloride and the alkane is isobutane. Other embodiments will be apparent from the ensuing description.

DESCRIPTION OF THE INVENTION

Figure 1:
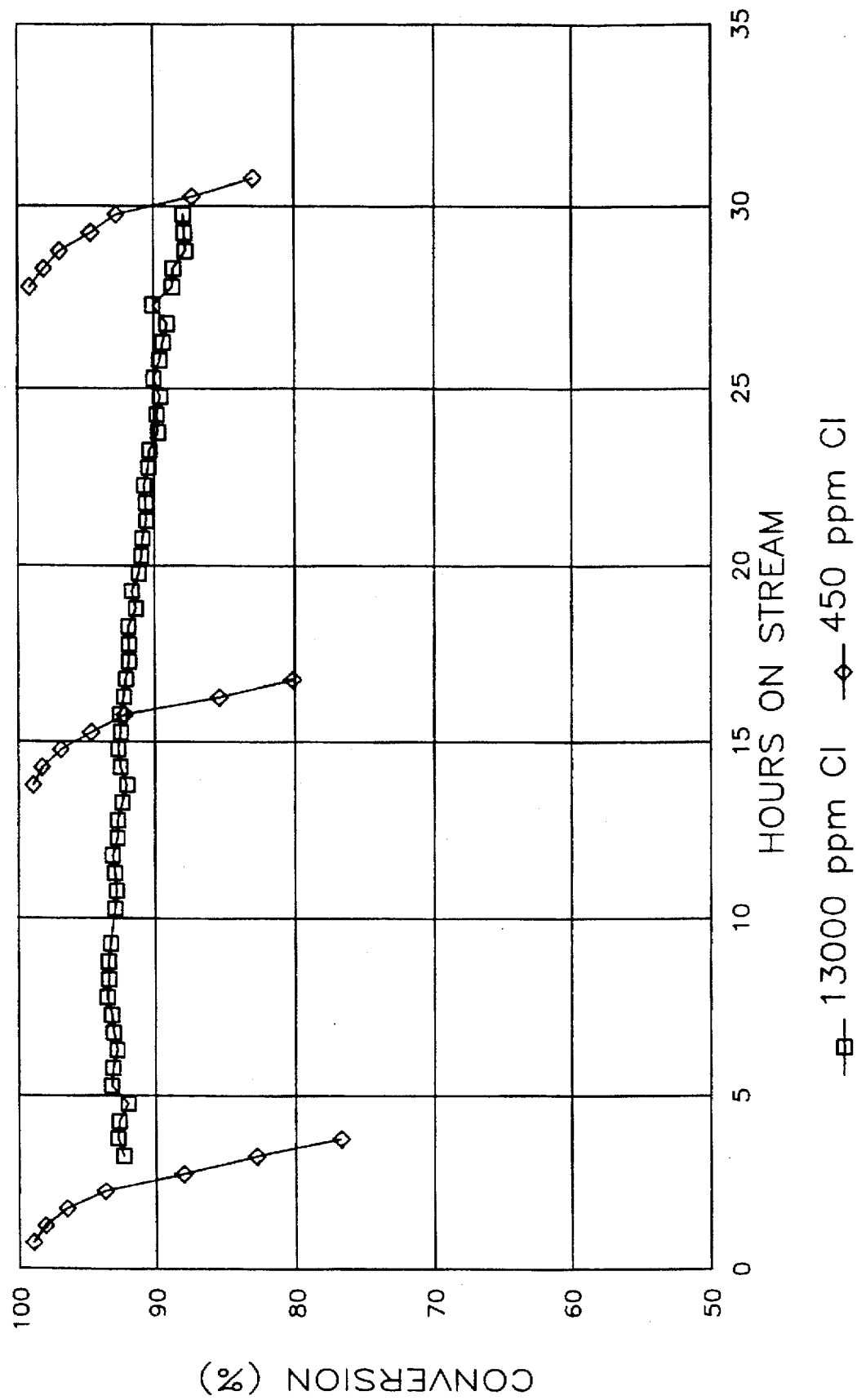
FIG. 1 graphically portrays catalyst deactivation in the alkylation of isobutane at 30°C using as the alkylating agent a) olefin in the presence of a minor amount of sec-butyl chloride and b) sec-butyl chloride only.

We have found that the dual problems of alkene oligomerization and catalyst instability attending the conventional alkylation process of alkenes by alkanes using solid acid catalysts can be circumvented using a modified process where the reactants are alkyl halides and alkanes. Our process is particularly operable with solid acid catalysts which are metal halides having strong Lewis acid properties which have reacted with the bound hydroxyl groups of refractory inorganic oxides and which also contain metal cations of the alkali or alkaline earth series. The nub of our invention is the reaction effecting alkylation using alkyl halides as a replacement for alkenes. The result is a process where catalyst lifetimes are increased by at least a factor of four, where the alkylate contains substantially less oligomers, and where the product alkylate is otherwise comparable to that produced in a conventional process.

The alkanes which may be used in the practice of our invention contain from 4 to 6 carbon atoms and the branched alkanes are particularly useful in the practice of our invention. Suitable alkanes are illustrated by n-butane, 2-methylpropane (commonly called isobutane), 2-methylbutane (or isopentane), 2,2-dimethylpropane (neopentane), n-pentane, n-hexane, 2,3-dimethylbutane, 2-methylpentane, 3-methylpentane, and 2,2-dimethylbutane.

In the conventional process of motor fuel alkylation the foregoing alkanes are reacted with alkenes, and those containing from 3 to 5 carbon atoms are of particular importance in this invention. Such alkenes include propene, butene-1, butene-2, isobutene, and the various isomeric pentenes such as pentene-1, pentene-2, 2-methylbutene-1, 2-methylbutene-2, 3-methylbutene-1, and so forth.

In our invention the aforementioned alkenes are replaced by alkyl halides which have from 3 up to about 5 carbon atoms. This is not to imply that higher alkyl halides are unreactive, but rather that the resulting alkylate is most useful as a motor fuel when the alkyl halide is in the designated carbon range. The chlorides and bromides are the most important of the alkyl halides in the practice of our invention, and alkyl chlorides are most important of all. Among the alkyl halides which may be used in the practice of this invention, as exemplified by the chlorides, are 1-chloropropane, 2-chloropropane, 1-chlorobutane, 2-chlorobutane, 1-chloro-2-methylpropane, 2-chloro-2-methylpropane, 1-chloropentane, 2-chloropentane, 3-chloropentane, 1-chloro-3-methylbutane, 2-chloro-3-methylbutane, 1-chloro-2-methylbutane, 2-chloro-2-methylbutane, and 1-chloro-2,2-dimethylpropane. Among the alkyl halides the secondary and tertiary alkyl halides are favored in the practice of this invention. Such halides, exemplified as their chlorides, are represented by 2-chloropropane, 2-chloro-2-methylpropane, 2-chlorobutane, 2-chloropentane, 3-chloropentane, 2-chloro-2-methylbutane, and 2-chloro-3-methylbutane. The alkane and alkyl halide used as reactants may be used in the same molar ratio as for the alkane and alkene,viz., a molar ratio of alkane to akyl halide from about 50:1 to as low as about 5:1, although it is preferred that they be used within the range of about 10:1 to about 30:1.

The reaction between alkanes and alkyl chlorides to form alkylate is catalyzed by solid acid catalysts. Catalytic composites which are particularly preferred comprise a refractory inorganic oxide, the reaction product of a first metal halide and bound surface hydroxyl groups of the refractory inorganic oxide, optionally, but preferably, a second metal cation, and optionally a zerovalent third metal, where the refractory inorganic oxide is selected from the group consisting of alumina, titania, zirconia, chromia, silica, boria, silica-alumina, aluminum phosphate, and combinations thereof, where said first metal halide is a fluoride, chloride, or bromide and the first metal is selected from the group consisting of aluminum, zirconium, tin, tantalum, titanium, gallium, antimony and boron, and where the second metal cation is a monovalent metal cation, especially alkali metal cations, or alkaline earth metal cations. The third metal is selected from the group consisting of platinum, palladium, nickel, ruthenium, rhodium, osmium and iridium, as well as combinations thereof, and is present optionally. The analogs of our catalyst without the metal cations are well known in the art (U.S. Pat. No. 2,999,074 and 3,318,820) and the extensive description of their preparation is applicable here with the exception of impregnation with a monovalent cation or alkaline earth metal cation. The following description then will suffice merely to afford the reader an understanding of our preferred catalytic composite.

The refractory inorganic oxides suitable for use in the preferred composites of this invention have a surface area of at least about 3 5 $m^2/g$, preferably greater than about 50 $m^2/g$, and more desirably greater than 100 $m^2/g$. There appears to be some advantage to working with materials having as high a surface area as possible, although exceptions are known which preclude making this a general statement. Suitable refractory inorganic oxides include alumina, titania, zirconia, chromia, silica, boria, silica-alumina, aluminum phosphate, and combinations thereof. Of these alumina is particularly preferred. Any alumina phase may be used so long as it has a surface area of at least 35 $m^2/g$ and has surface hydroxyl groups, which for all practical matters excludes alpha-alumina. Among the phases which may be used are included gamma-, etc-, and theta-alumina, although the various phases are not necessarily equivalent in their effectiveness as a motor fuel alkylation catalyst. Aluminum phosphate is another favored refractory material.

It is required that the refractory inorganic oxide have bound surface hydroxyl groups, by which is meant not adsorbed water but rather hydroxyl (OH) groups whose oxygen is bound to the metal of the inorganic oxide. These latter hydroxyl groups sometimes have been referred to as chemically combined hydroxyl. Since the presence of adsorbed water is generally detrimental to the preparation of the catalysts of our invention, the refractory inorganic oxides are first treated to remove surface hydroxyl groups arising from water, most usually by calcination at a temperature which specifically and preferentially removes physically adsorbed water without chemically altering the other hydroxyl groups. For example, calcination temperatures ranging from about 350°C to about 700°C are usually satisfactory where the inorganic oxide is alumina.

The catalytic composites optionally contain a metal having hydrogenation activity. Where a hydrogenation-active metal is present it generally is deposited on the refractory inorganic oxide prior to the reaction of its bound surface hydroxyl groups with metal halides. Although such a procedure has proven both convenient and effective, we do not wish to imply that this is the only sequence which may be used to afford an effective catalyst. Metals which have been found to be particularly effective include nickel and the noble metals of platinum, palladium, ruthenium, rhodium, osmium, and iridium, although platinum and palladium are by far the most desirable of the noble metals. The desired metal may be composited with the refractory inorganic oxide in any desired manner, such as by impregnation, coprecipitation, dipping, and so forth, of a suitable salt followed by reduction of the metal to its zerovalent state. Such methods are well known and need not be described here. Hydrogenation-active metal levels may range between about 0.01 up to about 1.0 weight percent for the noble metals, based on the weight of the finished catalyst, and from about 0.1 up to about 5 weight percent for nickel. The composite of the metal and refractory inorganic oxide is dried and calcined under controlled conditions to remove physically adsorbed water but under sufficiently mild conditions so that the "chemically combined" hydroxyl groups are not eliminated.

The more usual way of introducing a hydrogenation-active metal into the catalytic composites of our invention is by coimpregnation of the refractory inorganic oxide with a salt of the hydrogenation-active metal together with one or more monovalent or alkaline earth metal cations of our invention. But as stated above it is not believed that the particular procedure or sequence used is determinative of success of, or even of substantial significance to, the final catalytic composite.

The next stage in the preparation of our catalytic composites, whether or not a metal with hydrogenation activity has been deposited thereon, is to deposit on the composite one or more monovalent metal or alkaline earth metal cations. Such metals include lithium, sodium, potassium, cesium, rubidium, silver, copper(I), beryllium, magnesium, calcium, strontium, and barium. Among the monovalent metal cations the alkali metal cations are favored. The amount of metal cation which is impregnated on the composite is an amount having a gram atom equivalent from about 0.1 up to about 8 weight percent potassium, which is 0.0026 gram atoms potassium up to 0.2 gram atoms per 100 gram support. We define a "gram atom equivalent" of another metal cation as being a number of gram atoms of the metal divided by its valence per 100 grams support. For most divalent atoms the gram atom equivalent is 0.0013 up to about 0.1 gram atoms per 100 gram support.

There is some irregularity in the amount of metal cations which are to be impregnated upon the refractory inorganic oxides which are the supports in our invention. For the monovalent cations of lithium, potassium, cesium, rubidium, silver and copper, the amounts deposited are from 0.0026 to about 0.20 gram atom per 100 grams support; for sodium the amount is from 0.009 to about 0.20 gram atom per 100 grams support. For the divalent cations beryllium, strontium, and barium the amount is from 0.0013 to about 0.1 gram atoms per 100 gram support; for magnesium and calcium the amount is from 0.004 to about 0.1 gram atoms per 100 gram support. These amounts in terms of grams of metal cation per 100 gram support are summarized in the following table. Since the preferred range is from 0.012 up to about 0.12 gram atoms for monovalent cations, and 0.006 up to about 0.06 gram atoms for divalent metal cations, the preferred ranges also are listed in the following table.

TABLE

Amounts of Metal Cations on Supports (grams per 100 gram support)

| Metal Cation | Range | | Preferred Range | |
|---|---|---|---|---|
| | Minimum | Maximum | Minimum | Maximum |
| Monovalent | | | | |
| Lithium | 0.02 | 1.4 | 0.1 | 0.8 |
| Sodium | 0.2 | 4.6 | 0.3 | 2.8 |
| Potassium | 0.1 | 7.8 | 0.5 | 4.7 |
| Cesium | 0.3 | 26.6 | 1.6 | 15.9 |
| Rubidium | 0.2 | 17.1 | 1.0 | 10.3 |
| Copper (I) | 0.2 | 12.7 | 0.8 | 7.6 |
| Silver | 0.3 | 21.6 | 1.3 | 12.9 |
| Divalent | | | | |
| Beryllium | 0.01 | 0.9 | 0.1 | 0.5 |
| Magnesium | 0.1 | 2.4 | 0.1 | 1.5 |
| Calcium | 0.2 | 4.0 | 0.2 | 2.4 |
| Strontium | 0.1 | 8.8 | 0.5 | 5.3 |
| Barium | 0.2 | 13.7 | 0.8 | 8.2 |

Impregnation of the composite by the monovalent metal or alkaline earth metal cation may be done simply by mixing the composite with a suitable aqueous solution of the salt and removing water. The particular monovalent or alkaline earth metal salt used is not especially important so long as it provides sufficient solubility in water. As a practical matter, the halides, nitrates, and acetates may be the most commonly employed salts. Salts prone to precipitation should be avoided in order to avoid non-uniform impregnation, but otherwise there are no serious limitations on the salts which may be used. After evaporation of excess water, materials generally are dried at a temperature between about 100 and 200° C for 2–4 hours and then calcined at a temperature which specifically and preferentially removes physically adsorbed water without chemically altering the other hydroxyl groups. As mentioned before, temperatures ranging from about 350°C to about 700°C usually are satisfactory where the inorganic oxide is alumina.

Subsequent to metal deposition and calcination, the bound surface hydroxyl groups of the refractory inorganic oxide are reacted with a metal halide having Friedel-Crafts activity. Among the metals which may be used are included aluminum, zirconium, tin, tantalum, titanium, gallium, antimony, and boron. Suitable halides are the fluorides, chlorides, and bromides. Representative of such metal halides include aluminum chloride, aluminum bromide, ferric chloride, ferric bromide, zirconium chloride, zirconium bromide, boron trifluoride, titanium tetrachloride, gallium chloride, tin tetrachloride, antimony fluoride, tantalum chloride, tantalum fluoride, and so forth. Of these metal halides the aluminum halides are preferred, especially aluminum chloride. Except for boron trifluoride, the chlorides are generally the preferable halides.

The reaction between the metal halides of this invention and the bound surface hydroxyl groups of the refractory inorganic oxide is readily accomplished by, for example, sublimation or distillation of the metal halide onto the surface of the particles of the metal inorganic oxide composite. The reaction is attended by the elimination of between about 0.5 and 2.0 moles of hydrogen halide per mole of metal halide adsorbed thereon. The reaction temperature will depend upon such variables as the reactivity of the metal halides and its sublimation temperature or boiling point, where the metal halide is reacted in the gas phase, as well as on the nature of the refractory inorganic oxide. For example, using aluminum chloride and alumina as our specific examples reaction readily occurs within the range between about 190 through 600°C.

The amount of metal halide which is reacted with the bound surface hydroxyl groups of the refractory inorganic oxide is generally given in terms of the weight percent of the Friedel-Crafts metal on the composite. This amount will vary with the refractory inorganic oxide used, the relative number of bound surface hydroxyls of the inorganic oxide (which may be related to the particular oxide phase utilized), the specific Friedel-Crafts metal halide employed, as well as the particular procedure used to effect reaction between the Friedel-Crafts type metal halide and the bound surface hydroxyl. As a rough rule of thumb for aluminum chloride on alumina, as an example, the amount of aluminum chloride reacted expressed as weight percent aluminum in the final composite ranges from about 0.1 up to about 2.5%, with the level being a function primarily of the number of bound surface hydroxyl groups on the refractory inorganic oxide.

The reaction conditions for effecting alkylation clearly will depend upon the alkane and alkyl chloride used as well as the particular catalyst employed. Sufficient pressure is used to ensure a liquid phase reaction, but the pressure is otherwise unimportant as a reaction variable influencing the course of alkylation. Clearly the pressure necessary to maintain a liquid phase reaction depends upon the reaction temperature as well as the reactant, but pressures in the range of 100–1500 psig generally will suffice. Reaction temperatures may be as low as about −40°C and as high as about 150°C, depending upon the reactants as well as the particular solid acid catalyst used. For example, for the preferred catalyst described above temperatures between about 10° and about 50° C. generally will suffice and are preferred.

As alluded to above, the alkylation reaction is performed as a continuous reaction in the liquid phase. The catalytic composite generally is present as a fixed bed although this is not a necessary limitation but rather merely represents a convenient reaction mode. A feedstock containing a mixture of alkyl chlorides having from 3 up through about 5 carbon atoms and alkanes having from 4 up through about 6 carbon atoms is passed in the liquid phase over the catalyst maintained at a temperature between about −10° and about 150° C. The reaction may be run in either an upflow or a downflow mode and the mode selected is a matter of choice. The feedstock generally is passed over the catalyst at a liquid hourly space velocity between about 0.5 and about 5.0/hr.

As stated previously, the effect of substituting alkyl halide for an alkene of the same carbon number is to increase the lifetime of the catalyst under comparable reaction conditions by a factor of at least four. By catalyst "lifetime" is meant the period during which conversion of olefin (or alkyl halide) is at least 90%, i.e, the time interval at unvarying reaction conditions during which the extent of olefin or alkyl halide conversion drops from 100% to 90%. It also is to be noted that the use of alkyl halides with the catalysts of our invention afford substantially less oligomeric products in the alkylate than are formed when olefins are the alkylating agent, thus the alkyl halide is utilized virtually exclusively in alkylation rather than being diverted to side products.

The following examples are merely illustrative of our invention and are not intended to limit it in any way.

EXAMPLE 1

Alkylation with Sec-Butyl Chloride. A catalyst (16.4 g) prepared by subliming $AlCl_3$ onto a support consisting of 0.25 weight percent Pt and 1.0 weight percent K on an extruded gamma alumina base was loaded into a ⅞" ID stainless steel reactor under a $N_2$ stream to avoid any contact with moisture. The catalyst was pretreated with $H_2$ at 350°C for 2 hours, then cooled to 30°C and flushed with liquid isobutane at 450 psig, 150 g/hr for 2 hours. After completion of the flush, an isobutane/secondary butylchloride feedstock with a molar ratio of 45/1 (13000 wt. ppm Cl) was cut into the plant at 92 g/hr while maintaining the temperature and pressure. This feed was maintained for 30 hours. FIG. 1 shows that during this period the conversion fell from about 93% to 88%. Greater than 2 g of $C_{5+}$ products were recovered per gram of butene equivalent (i.e., the amount of sec-butyl chloride containing as many moles as 1 g butene) converted through the entire 30 hour period indicating that paraffin alkylation was predominant. Virtually identical results were obtained using tert-butyl chloride in place of the sec-butyl chloride.

EXAMPLE 2

Alkylation with Olefin in the Presence of Alkyl Chloride. The same catalyst as in Example 1 was pretreated with $H_2$ and flushed with isobutane using the same procedure, except that the isobutane flush also contained 450 weight ppm Cl as secondary butylchloride. After completion of the flush an isobutane/2-butene/secondary butylchloride feed with a molar ratio of 45/1/0.03 (450 weight ppm Cl) was cut into the plant and maintained for 4 hours. FIG. 1 shows that conversion fell from about 99% to 77% over this period. The gram of $C_{5+}$ products produced per gram of butene converted dropped from 2.0 to 1.8 over this time indicating that olefin oligomerization was increasing as the catalyst deactivated. The catalyst was regenerated by stripping with $H_2$ at 130°C for 4 hours, followed by an isobutane/secondary butylchloride flush at 30°C for 2 hours. FIG. 1 shows that two additional cycles afforded results comparable to the first cycle.

These examples demonstrate the substantial benefit in catalyst stability that is obtained in paraffin alkylation by the use of an alkylchloride feed as opposed to a feed consisting of an olefin with trace levels of alkylchloride. In addition, in the case of an alkylchloride feed the observed products appear to arise predominantly from the desired paraffin alkylation reaction, whereas olefin oligomerization appears to become significant in the case of an olefin feed, particularly at lower conversion levels.

What is claimed is:

1. A process for increasing by a factor of at least four the lifetime of a solid acid catalyst effecting alkylation of from 5 up to about 50 molar proportions of an alkane having from 4 up to about 6 carbon atoms with one molar proportion of an alkene having from 3 up to about 5 carbon atoms, where said solid acid catalyst comprises: a) a refractory inorganic oxide, b) the reaction product of a first metal halide and bound surface hydroxyl groups of said refractory inorganic oxide, c) a second metal cation, and d) optionally a zerovalent third metal; where said refractory inorganic oxide is selected from the group consisting of alumina, titania, zirconia, chromia, silica, boria, silica-alumina, and combinations thereof; said first metal halide is a fluoride, chloride, or bromide and the first metal is selected from the group consisting of aluminum, gallium, zirconium and boron; said second metal cation is selected from the group consisting of i) monovalent metal cations in an amount from 0.0026 up to about 0.20 gram atoms per 100 grams refractory inorganic oxide for lithium, potassium, cerium, rubidium, silver, and copper, and in an amount from 0.012 to about 0.12 gram atoms for sodium, and (ii) alkaline earth metal cations in an amount from about 0.0013 up to about 0.01 gram atoms per 100 grams of refractory inorganic oxide for beryllium, strontium, and barium, and an amount from about 0.004 up to about 0.1 gram atoms per 100 grams support for magnesium and calcium; and any combination thereof; and said third metal is selected from the group consisting of platinum, palladium, nickel, ruthenium, rhodium, osmium and iridium, and any combination thereof, said process comprising replacing said alkene with an equimolar proportion of an alkyl halide having the same number of carbon atoms.

2. The process of claim 1 where the alkyl halide is a butyl halide.

3. The process of claim 2 where the butyl halide is a secondary or tertiary butyl halide.

4. The process of claim 1 where the alkyl halide is a secondary or tertiary alkyl halide.

5. The process of claim 1 where the halide is a chloride or a bromide.

6. The process of claim 1 where the alkane is a butane.

7. The process of claim 6 where the butane is isobutane.

8. The process of claim 1 where the ratio of alkane to alkyl halide is from about 10 to about 30.

9. The process of claim 1 where the refractory inorganic oxide is alumina, the first metal halide is aluminum chloride, and the second metal cation is potassium cation.

10. The process of claim 1 where the alkyl halide is tert-butyl chloride and the alkane is isobutane.

11. The process of claim 1 where the alkane is a branched alkane.

12. The process of claim 1 where reaction conditions include a temperature from about −40° up to about 150°C.

* * * * *